(12) United States Patent
Benezech et al.

(10) Patent No.: US 6,235,059 B1
(45) Date of Patent: May 22, 2001

(54) INTERSOMATIC SETTING AND FUSION SYSTEM

(75) Inventors: Jacques Benezech, Montpellier; Albert Alby, Paris, both of (FR)

(73) Assignee: Scient'x (Societe a Responsabilite Limitee) (FR)

( * ) Notice: Subject to any disclaimer, the term of this patent is extended or adjusted under 35 U.S.C. 154(b) by 0 days.

(21) Appl. No.: 09/147,083
(22) PCT Filed: Apr. 2, 1997
(86) PCT No.: PCT/FR97/00591
    § 371 Date: Dec. 2, 1998
    § 102(e) Date: Dec. 2, 1998
(87) PCT Pub. No.: WO97/37620
    PCT Pub. Date: Oct. 16, 1997

(30) Foreign Application Priority Data

Apr. 3, 1996 (FR) .................................................. 96 04196

(51) Int. Cl.[7] ........................................................ A61F 2/44
(52) U.S. Cl. ............................................. 623/17.16; 606/61
(58) Field of Search ................................ 623/17, 17.16; 606/61

(56) References Cited

U.S. PATENT DOCUMENTS 5,147,361 * 9/1992 Ojima et al. ............................ 623/17
5,683,463 * 11/1997 Godefroy et al. ...................... 623/17
5,702,453 * 12/1997 Rabbe et al. ........................... 623/17

FOREIGN PATENT DOCUMENTS 0 179 695 * 4/1986 (EP) .
0 493 698 * 7/1992 (EP) .
2 703 580 * 10/1994 (FR) .

* cited by examiner

Primary Examiner—David H. Willse
Assistant Examiner—Choon P. Koh
(74) Attorney, Agent, or Firm—Bacon & Thomas PLLC

(57) ABSTRACT

A system for intersomatic fusion and setting of vertebrae. The system includes at least one open internal cage arranged for receiving spongy bone or bone substitute and is designed to be interposed between two vertebrae during diskectomy. The cage (1) includes on its anterior face (5) an external element forming a plate (12) extending in a plane substantially perpendicular to the insertion plane of the cage (1), and has at each of its ends an anchor device (13,14) adapted for anchoring to at least two adjacent vertebrae to be secured to each other by the cage (1). The system can be separated into two parts, the cage and the plate.

9 Claims, 2 Drawing Sheets

INTERSOMATIC SETTING AND FUSION SYSTEM

BACKGROUND OF THE INVENTION

1. Field of the Invention

The present invention relates to an intersomatic fusion and setting system for vertebrae. The system includes at least one open internal cage receiving spongy bone and designed to be interposed between two vertebrae during diskectomy and the system is capable of installing a bone graft or material encouraging intersomatic fusion, thereby encouraging fusion between the two vertebrae concerned.

2. Description of Related Art

Similar cages are known, for example, from the following patent applications: FR 2 703 580; EP 493 698; EP 599 419; FR 2 124 815; EP 307 241; EP 615 428.

These cages are generally ovoid or parallelepipedal in shape. They are rigid, made of metal or of a biocompatible material, and designed to receive spongy bone via open top and bottom faces.

Although cages of the above type generally give good results, it is nevertheless true that in some cases it is necessary to position the cage and to ensure that it cannot move so as to be sure of avoiding any possible migration or risk of secondary displacement of the cage.

A prosthesis is also known from document EP 0 179 695 comprising an implant forming an open internal cage designed to receive spongy bone or bone substitute. The cage is fitted with a plate extending in a plane substantially perpendicular to the insertion plane of the cage, having two holes on either side thereof for passing respective screws for anchoring in each of the two adjacent vertebrae that are to be secured together. The implant which is in the form of a length of a cylinder is designed to be inserted between two adjacent vertebrae from which portions of the vertebral bodies have been removed. Such a prosthesis has a drawback concerning the anchor screws which are subjected to large forces that can cause the screws to become at least partially disconnected from the vertebrae, and thus allowing the cage to be relatively mobile.

SUMMARY OF THE INVENTION

The object of the invention is to remedy the drawbacks of the prior art by proposing an intersomatic fusion and setting system for vertebrae, the system being of the type comprising:

- at least one open internal cage arranged for receiving spongy bone or bone substitute and designed to be interposed between two vertebrae during diskectomy; and
- an external plate extending in a plane substantially perpendicular to the insertion plane of the cage, on either side thereof, and having an anchor device adapted for anchoring at least to the two adjacent vertebrae that is to be secured together by the cage.

According to the invention, the setting system has an anterior wall, a posterior wall, and side walls forming a rigid parallelepiped of shape and profile which are adapted to the intervertebral space defined by two adjacent vertebrae.

The cage is rigid, made of metal or biocompatible plastics material, generally parallelepipedal in shape, and adapted to the intervertebral space, and it is designed to receive spongy bone or bone substitute material via its top and bottom open faces and/or via a front opening.

Depending on requirements, the system of the invention is made either in the form of a single piece cage-and-plate unit or in the form of an internal cage and an external plate including devices for assembling the plate to the cage.

The present invention also relates to characteristics which appear from the following description and which should be considered in isolation or in any technically feasible combination.

BRIEF DESCRIPTION OF THE DRAWING

The description is given by way of non-limiting example making it better understood how the invention can be performed, and is given with reference to the accompanying drawings, in which.

Figure 1:
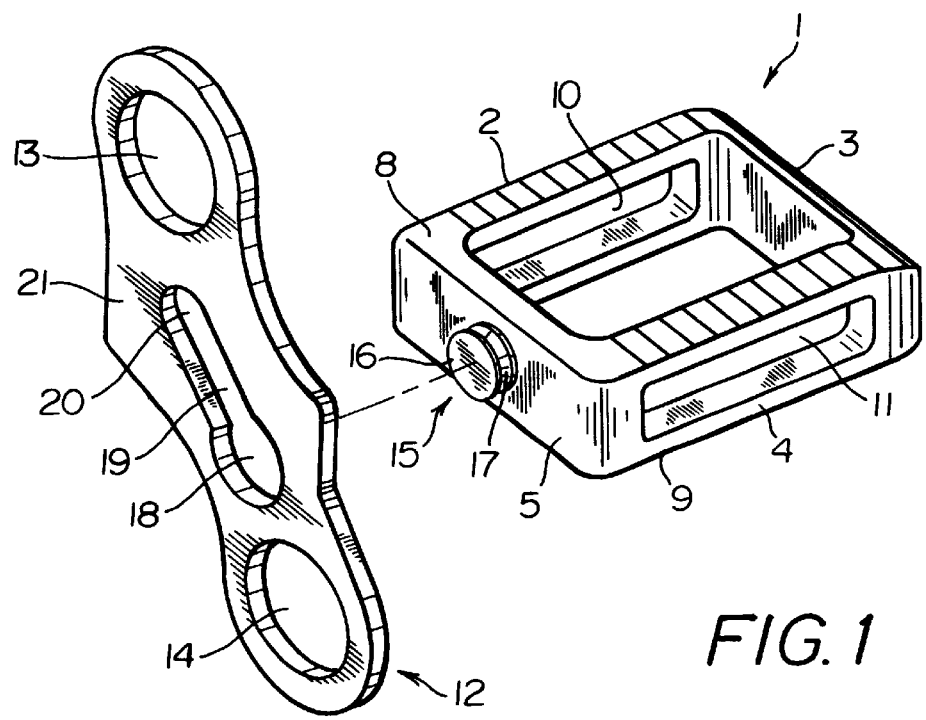
FIG. 1 is an exploded perspective view of a first embodiment of a setting system of the invention.

By way of non-limiting example, the cage 1 shown in FIG. 1 generally includes a rigid parallelepiped shape whose side walls 2, 3, 4, and 5 are designed to hold spongy bone or bone substitute captive and whose top and bottom faces 8 and 9 are open towards two successive vertebrae.

DETAILED DESCRIPTION OF THE PREFERRED EMBODIMENTS

The anterior or front face 5 and posterior face 3 are of heights that are determined so as to conserve an appropriate intervertebral space.

Still in the present example, the side walls 2 and 4 of the cage 1 are provided with large slots 10 and 11 of shape similar to the shapes of the corresponding side walls 2 and 4 through which they pass.

The cage 1 is provided with openings through four of its faces. The cage 1 also carries on its anterior or front face 5 an external strap-forming element, external strap or plate 12 (referred below to as a "plate") extending in a plane that is substantially perpendicular to the insertion plane of the cage 1, on either side thereof, and having at each of its ends anchor devices or fixing holes 13 and 14 for anchoring to at least two adjacent vertebrae in order to connect them together via the cage 1.

Naturally, the external strap or plate 12 could be integrally formed with the internal cage 1, e.g. by molding or casting the cage-and-plate unit.

Nevertheless, it is preferred in the present embodiment to present a plate 12 and an internal cage 1 that are made separately and that are secured to each other subsequently by various and known assembly methods.

Still in the example of FIG. 1, the assembly of the plate 12 on the cage 1 is enabled by a cylindrical stud 15 made on a vertical anterior is enabled face 5 of the cage 1 and a peripheral groove 17 that is formed beneath the circular head 16 of the stud 15, the head 16 is suitable for being inserted in a corresponding enlarged portion 18 of a keyhole-shaped oblong slot 19 formed through the plate 12, with the groove 17 being of a size suitable for sliding between the side edges of the narrow zone 20 of the keyhole-shaped oblong slot 19 until the head 16 of the stud 15 co-operates with the outside face 21 of the plate 12 to provide axial locking.

The engagement of the stud in the keyhole may be designed to require the stud to be forced into the narrow zone.

Naturally, the above-described cage can have various dimensions in height, in width, and in depth.

As in the following example, it may also be given a preferred anatomical shape.

It can also be assumed that the spongy bone or other bone substitute is put into place either before or after the cage 1 has been positioned between the vertebrae.

Figure 2:
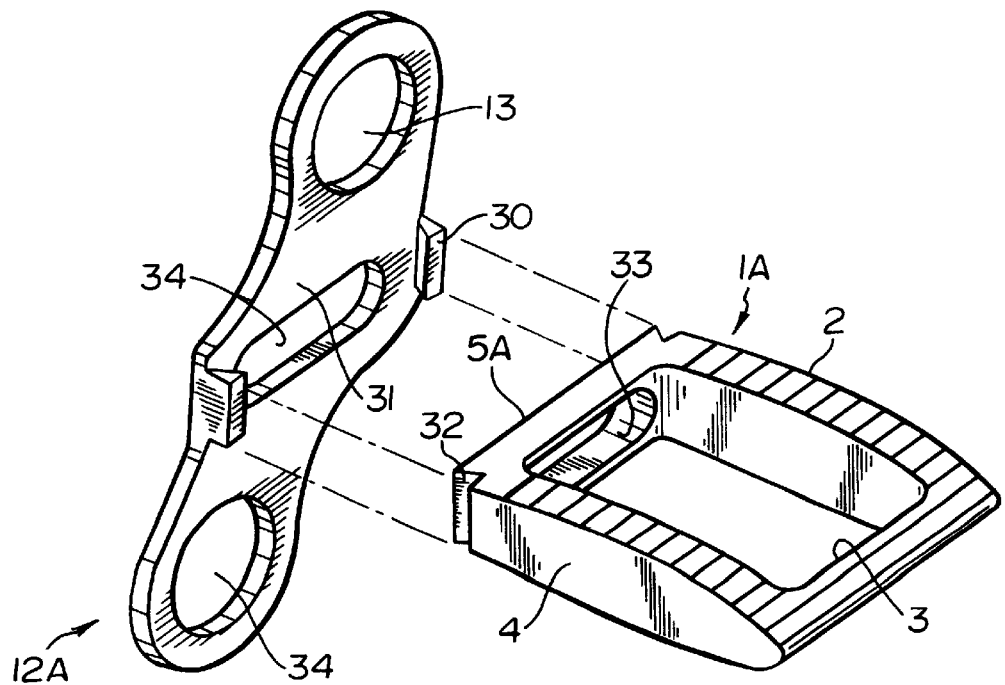
FIG. 2 is an exploded perspective view of a second embodiment of a setting system of the invention.

The embodiment shown in FIG. 2 differs from the preceding embodiment essentially in the assembly of the plate 12A to the cage 1A, the assembly including a dovetail-shaped slideway whose mortise-forming portion 30 is made on an inside face 31 of the plate 12A for sliding in a vertical direction while the corresponding tenon-forming portion 32 is formed on the outside front face 5A of the cage 1A, or vice versa.

It will be observed that in the present embodiment, the cage 1A does not have lateral openings as in the preceding example.

The outside front face 5A of the cage 1A and the corresponding inside face 31 of the plate 12A with which it co-operates have respective identical oblong slots 33 and 34 designed to be brought into coincidence when the plate 12A is assembled on the cage 1A so as to enable spongy bone to be inserted frontally after the cage 1A has been put into place.

It should also be observed that the special profile and shape of the cage 1A in the example of FIG. 2 enable the overall device to fit perfectly in the intervertebral space.

Figure 3:
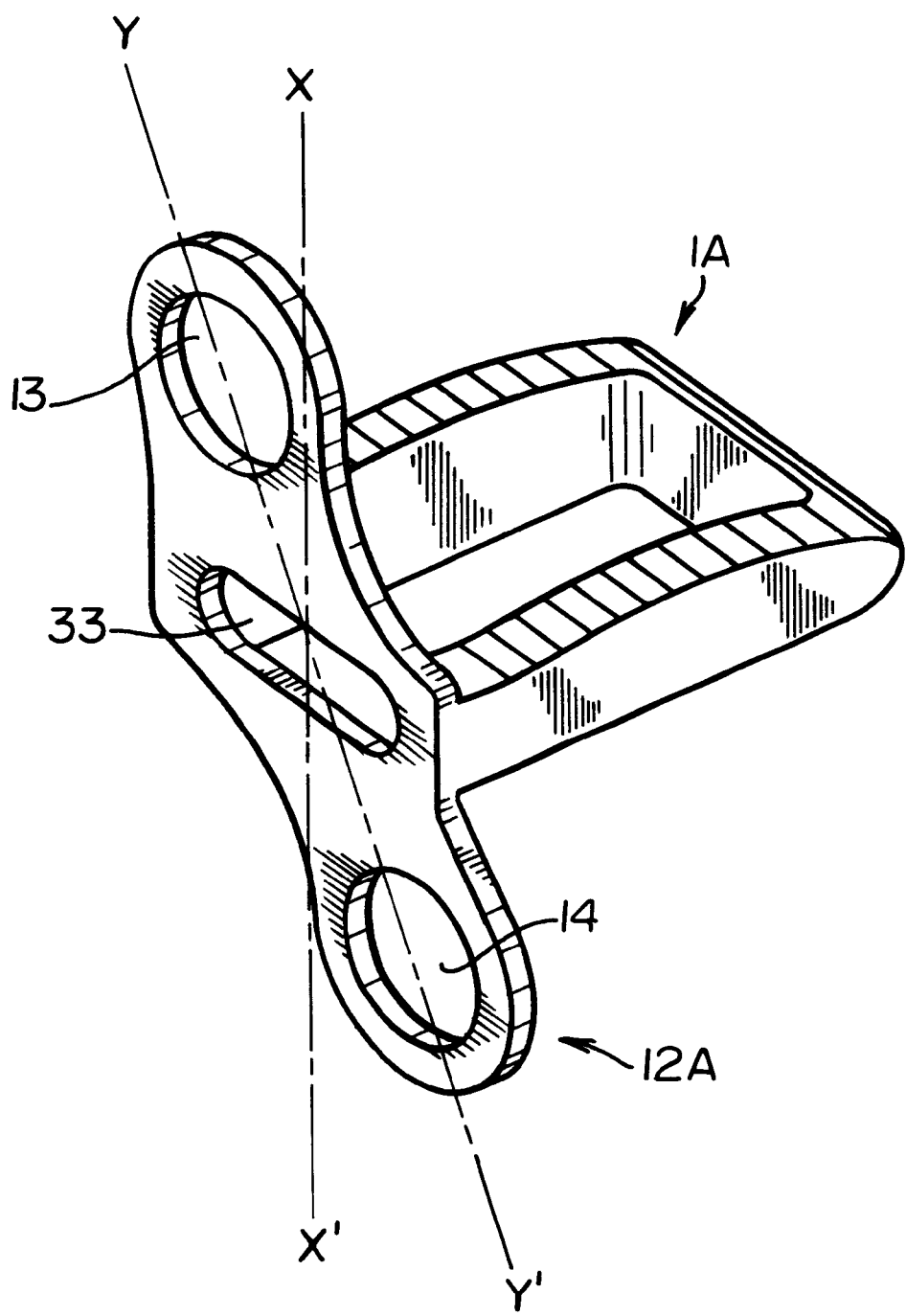
FIG. 3 is a view of a one-piece setting system.

The embodiment shown in FIG. 3 differs from that of FIG. 2 in that it is made as a single piece.

The anterior face 5A of the cage-and-plate unit has an oblong slot 33 so as to enable spongy bone to be inserted frontally into the cage portion after the cage-and-plate unit has been put into place.

In a manner that is common to the above-described embodiments of FIGS. 1, 2, and 3, the anchor device for anchoring the plate 12, 12A on the vertebrae, after the cage 1, 1A has been fixed make use of pedicular screws (not shown) passing through corresponding holes 13 and 14 formed through the ends of the strap 12, 12A.

According to another characteristic of the invention, it should be observed that the fixing holes 13 and 14 of the plate 12, 12A are disposed on opposite sides of a central vertical axis X, X' of the assembly on a diagonal Y, Y'.

In an embodiment (not shown) the setting system can implement two or more internal cages 1, 1A which are secured to one another and relative to three or more successive vertebrae by a plate 12, 12A having two assembly devices 15, 18 or 30, 32 with the cages 1, 1A, and two end fixing holes 13, 14, and also an intermediate fixing hole co-operating with three or more pedicular screws for anchoring in the vertebrae.

The plates are shown as having one fixing screw per vertebra, however they could have more, e.g. two.

Naturally the setting system can also be constituted by two or more cage-and-plate units as defined in the examples of FIGS. 1, 2, or 3 interconnected in pairs by said plates which may optionally overlap.

Setting systems of the invention are preferably made of titanium alloy or an equivalent material or else of a biocompatible plastics material.

The present invention is by no means restricted to the above-described preferred embodiments, but covers all variations that might be implemented by using equivalent functional elements or devices that would be apparent to a person skilled in the art, or modifications that fall within the spirit and scope of the appended claims.

What is claimed is:

1. An intersomatic fusion and setting system for vertebrae comprising:
   at least one open internal case arranged for receiving spongy bone or bone substitute and designed to be interposed between two adjacent vertebrae during diskectomy;
   an external plate extending in a plane substantially perpendicular to an insertion plane of the cage, on either side thereof, the external plate having an anchor device adapted for anchoring the cage to at least to two adjacent vertebrae that are to be secured together by the cage, wherein said external plate is configured to be selectively attached to said cage; and
   wherein the cage has an anterior wall, a posterior wall, and side walls that form a rigid parallelepiped shape and profile that are customized for placement in a intervertebral space between two adjacent vertebrae.

2. The system according to claim 1, wherein the anterior wall (5) of the cage has an opening that permits spongy bone to be inserted frontally into the cage.

3. The system according to claim 1, wherein the anchor device is comprised of respective single holes that are configured for passing respective screws designed to be engaged in a facing vertebra, said holes being disposed on a diagonal on either side of a central vertical axis of the assembly.

4. The system according to claim 1, wherein the external plate and the internal cage are a single piece.

5. The system according to claim 1, wherein the external plate and the internal cage are made separately and are secured to each other.

6. The system according to claim 5, wherein the plate is secured on the cage by a dovetail slideway having a mortice-forming portion that is formed on an inside face of the plate in a vertical sliding direction and a corresponding tennon portion is formed on an outside front face of the cage, or vice versa.

7. The system according to claim 6, wherein the outside front face of the cage and the corresponding inside face of the plate with which it co-operates having respective identical oblong slots designed to be placed into coincidence when the plate is assembled to the cage in order to enable spongy bone or bone substitute to be inserted frontally after the cage has been put into place between adjacent vertebrae.

8. The system according to claim 1, wherein the internal cage (1A), further includes open top and bottom faces and the side walls are provided with insertion slots that are adapted for insertion of spongy bone or bone substitute.

9. The system according to claim 1, wherein two or more of the internal cages are secured to one another and positioned relative to three or more successive vertebrae by the plate, the plate having at least two assembly devices arranged for being assembled to said cages, and at least two end fixing holes, and an intermediate fixing hole, said fixing holes co-operating with three or more pedicular screws that anchor into the vertebrae.

* * * * *